US010494655B2

United States Patent
Vinodh Kumar et al.

(10) Patent No.: US 10,494,655 B2
(45) Date of Patent: Dec. 3, 2019

(54) SYNTHETIC FUSION GENE AND ITS USE THEREOF

(71) Applicant: UNIVERSITI BRUNEI DARUSSALAM, Gadong (BN)

(72) Inventors: Prabitha Vinodh Kumar, Gadong (BN); Zohrah Sulaiman, Gadong (BN)

(73) Assignee: UNIVERSITI BRUNEI DARUSSALAM, Gadong (BN)

( * ) Notice: Subject to any disclaimer, the term of this patent is extended or adjusted under 35 U.S.C. 154(b) by 318 days.

(21) Appl. No.: 15/301,520

(22) PCT Filed: Apr. 1, 2015

(86) PCT No.: PCT/IB2015/052385
§ 371 (c)(1),
(2) Date: Oct. 3, 2016

(87) PCT Pub. No.: WO2015/151038
PCT Pub. Date: Oct. 8, 2015

(65) Prior Publication Data
US 2019/0153487 A1     May 23, 2019

(30) Foreign Application Priority Data
Apr. 3, 2014 (BN) .................. BN/N/2014/0037

(51) Int. Cl.
| | | |
|---|---|---|
| C12P 7/64 | (2006.01) | |
| C12N 15/62 | (2006.01) | |
| C12P 19/02 | (2006.01) | |
| C12P 19/14 | (2006.01) | |
| C12N 9/42 | (2006.01) | |
| C12N 9/02 | (2006.01) | |

(52) U.S. Cl.
CPC ............ *C12P 7/649* (2013.01); *C12N 9/0071* (2013.01); *C12N 9/2437* (2013.01); *C12N 15/62* (2013.01); *C12P 19/02* (2013.01); *C12P 19/14* (2013.01); *C12Y 114/18001* (2013.01); *C12Y 302/01004* (2013.01); *C07K 2319/00* (2013.01); *C12P 2201/00* (2013.01)

(58) Field of Classification Search
CPC ...... C12P 7/649; C12P 2201/00; C12N 15/62; C12N 9/2437; C12N 9/0071; C07K 2319/00; C12Y 302/01004; C12Y 114/18001
See application file for complete search history.

(56) References Cited

U.S. PATENT DOCUMENTS

| | | |
|---|---|---|
| 7,981,650 B2 | 7/2011 | Levasseur et al. |
| 2012/0083012 A1 | 4/2012 | Chang et al. |

FOREIGN PATENT DOCUMENTS

| | | |
|---|---|---|
| WO | WO 2005/093050 | 10/2005 |
| WO | WO 2007/094852 | 8/2007 |
| WO | WO 2011/153276 | 12/2011 |

OTHER PUBLICATIONS

Curach et al., Isolation, characterization and expression of the hex1 gene from Trichoderma reesei. Gene, 2004, vol. 331: 133-140. (Year: 2004).*
Kisselev L., Polypeptide release factors in prokaryotes and eukaryotes: same function, different structure. Structure, 2002, vol. 10: 8-9. (Year: 2001).*
Moussa TAA., Cloning and sequncing of phenol oxidase 1 (pox1) gene from Pleurotus ostreatus. African J. Biotechnol., 2011, vol. 10(8): 1299-1308. (Year: 2011).*
Prabitha Vinodh Kumar & Zohrah Sulaiman., Use of synthetic fusion gene to produce biodiesel from lignocellulosic biomass. Biofuels, 2016, vol. 7(2): 191-200. (Year: 2016).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Kim, H.M et al., Improving lignocellulose degradation using xylanase-cellulase fusionprotein with a glycine-serine linker, International Journal . . . Dec. 3, 2014, vol. 73.

* cited by examiner

*Primary Examiner* — Ganapathirama Raghu
(74) *Attorney, Agent, or Firm* — Sinorica, LLC

(57) ABSTRACT

The present invention discloses synthetic fusion gene comprising hex1 and pox1 genes, their process of preparation, polypeptide(s) encoded by the same and its use thereof for biological pre-treatment of biomass for the production of biodiesel.

6 Claims, 12 Drawing Sheets
Specification includes a Sequence Listing.

Customer        Universiti Brunei Darussalam, Prabitha Kumar

Name of the gene    pox1_and_hex1
optimized for        Escherichia coli

```
                                              SacI    MfeI
        CACTATAGGGCGAATTGAAGGAAGGCCGTCAAGGCCGCATGAGCTCCAATTGATGTTTCC
    1   ---------+---------+---------+---------+---------+---------+
        GTGATATCCCGCTTAACTTCCTTCCGGCAGTTCCGGCGTACTCGAGGTTAACTACAAAGG
                                                          M  F  P

GGGTGCACGTATTCTGGCAACCCTGACCCTGGCACTGCATCTGCTGCATGGCACCCATGC
   61   ---------+---------+---------+---------+---------+---------+
        CCCACGTGCATAAGACCGTTGGGACTGGGACCGTGACGTAGACGACGTACCGTGGGTACG
         G  A  R  I  L  A  T  L  T  L  A  L  H  L  L  H  G  T  H  A

AgeI                HincII
        AGCCATTGGTCCGACCGGTGATATGTATATTGTTAACGAAGATGTTAGTCCGGATGGTTT
  121   ---------+---------+---------+---------+---------+---------+
        TCGGTAACCAGGCTGGCCACTATACATATAACAATTGCTTCTACAATCAGGCCTACCAAA
         A  I  G  P  T  G  D  M  Y  I  V  N  E  D  V  S  P  D  G  F TACCCGTAGCGCAGTTGTTGCACGTAGCGATCCGACCACCAATGGCACCAGCGAAACCCT
  181   ---------+---------+---------+---------+---------+---------+
        ATGGGCATCGCGTCAACAACGTGCATCGCTAGGCTGGTGGTTACCGTGGTCGCTTTGGGA
         T  R  S  A  V  V  A  R  S  D  P  T  T  N  G  T  S  E  T  L PvuII              PvuII
        GACAGGTGTTCTGGTTCAGGGTAATAAAGGTGATAATTTCCAGCTGAATGTGCTGAATCA
  241   ---------+---------+---------+---------+---------+---------+
        CTGTCCACAAGACCAAGTCCCATTATTTCCACTATTAAAGGTCGACTTACACGACTTAGT
         T  G  V  L  V  Q  G  N  K  G  D  N  F  Q  L  N  V  L  N  Q
```

FIG. 2A

```
        GCTGAGCGATACCACCATGCTGAAAACCACCAGTATTCATTGGCATGGTTTTTTTCAGAG
301     ---------+---------+---------+---------+---------+---------+
        CGACTCGCTATGGTGGTACGACTTTTGGTGGTCATAAGTAACCGTACCAAAAAAAGTCTC
         L   S   D   T   T   M   L   K   T   T   S   I   H   W   H   G   F   F   Q   S

CGGTAGCACCTGGGCAGATGGTCCGGCATTTGTTAATCAGTGTCCGATTGCAAGCGGTAA
361     ---------+---------+---------+---------+---------+---------+
        GCCATCGTGGACCCGTCTACCAGGCCGTAAACAATTAGTCACAGGCTAACGTTCGCCATT
         G   S   T   W   A   D   G   P   A   F   V   N   Q   C   P   I   A   S   G   N

CAGCTTTCTGTATGATTTTAATGTTCCGGATCAGGCAGGCACCTTTTGGTATCATAGCCA
421     ---------+---------+---------+---------+---------+---------+
        GTCGAAAGACATACTAAAATTACAAGGCCTAGTCCGTCCGTGGAAAACCATAGTATCGGT
         S   F   L   Y   D   F   N   V   P   D   Q   A   G   T   F   W   Y   H   S   H

TCTGAGCACCCAGTATTGTGATGGTCTGCGTGGTCCGTTTATTGTTTATGATCCGAGCGA
481     ---------+---------+---------+---------+---------+---------+
        AGACTCGTGGGTCATAACACTACCAGACGCACCAGGCAAATAACAAATACTAGGCTCGCT
         L   S   T   Q   Y   C   D   G   L   R   G   P   F   I   V   Y   D   P   S   D

TCCGCATCTGAGCCTGTATGATGTTGATAATGCAGATACCATTATCACCCTGGAAGATTG
541     ---------+---------+---------+---------+---------+---------+
        AGGCGTAGACTCGGACATACTACAACTATTACGTCTATGGTAATAGTGGGACCTTCTAAC
         P   H   L   S   L   Y   D   V   D   N   A   D   T   I   I   T   L   E   D   W

GTATCACGTTGTGGCACCGCAGAATGCCGTTCTGCCGACCGCAGATAGCACCCTGATTAA
601     ---------+---------+---------+---------+---------+---------+
        CATAGTGCAACACCGTGGCGTCTTACGGCAAGACGGCTGGCGTCTATCGTGGGACTAATT
         Y   H   V   V   A   P   Q   N   A   V   L   P   T   A   D   S   T   L   I   N

TGGTAAAGGTCGTTTTGCAGGCGGTCCGACCAGCGCACTGGCAGTTATTAATGTTGAAAG
661     ---------+---------+---------+---------+---------+---------+
        ACCATTTCCAGCAAAACGTCCGCCAGGCTGGTCGCGTGACCGTCAATAATTACAACTTTC
         G   K   G   R   F   A   G   G   P   T   S   A   L   A   V   I   N   V   E   S
```

FIG. 2B

```
     CAATAAACGCTATCGCTTTCGCCTGATTAGCATGAGCTGTGATCCGAACTTTACCTTTAG
721  ---------+---------+---------+---------+---------+---------+
     GTTATTTGCGATAGCGAAAGCGGACTAATCGTACTCGACACTAGGCTTGAAATGGAAATC
      N   K   R   Y   R   F   R   L   I   S   M   S   C   D   P   N   F   T   F   S
```

```
                           PstI
                         BspMI
     CATTGATGGTCATAGCCTGCAGGTTATTGAAGCAGATGCCGTTAATATTGTTCCGATTGT
781  ---------+---------+---------+---------+---------+---------+
     GTAACTACCAGTATCGGACGTCCAATAACTTCGTCTACGGCAATTATAACAAGGCTAACA
      I   D   G   H   S   L   Q   V   I   E   A   D   A   V   N   I   V   P   I   V
```

```
                                BspMI
     TGTTGATAGCATCCAGATTTTTGCAGGTCAGCGTTATAGCTTTGTTCTGAATGCAAATCA
841  ---------+---------+---------+---------+---------+---------+
     ACAACTATCGTAGGTCTAAAAACGTCCAGTCGCAATATCGAAACAAGACTTACGTTTAGT
      V   D   S   I   Q   I   F   A   G   Q   R   Y   S   F   V   L   N   A   N   Q
```

```
                                                     AgeI
     GACCGTGGATAACTATTGGATTCGTGCAGATCCGAATCTGGGTAGCACCGGTTTTGATGG
901  ---------+---------+---------+---------+---------+---------+
     CTGGCACCTATTGATAACCTAAGCACGTCTAGGCTTAGACCCATCGTGGCCAAAACTACC
      T   V   D   N   Y   W   I   R   A   D   P   N   L   G   S   T   G   F   D   G
```

```
     TGGCATTAATAGCGCAATTCTGCGTTATGCCGGTGCAACCGAAGATGATCCGACAACCAC
961  ---------+---------+---------+---------+---------+---------+
     ACCGTAATTATCGCGTTAAGACGCAATACGGCCACGTTGGCTTCTACTAGGCTGTTGGTG
      G   I   N   S   A   I   L   R   Y   A   G   A   T   E   D   D   P   T   T   T
```

```
      CTCAAGCACCAGCACACCGCTGGAAGAAACCAATCTGGTTCCGCTGGAAAATCCTGGTGC
1021  ---------+---------+---------+---------+---------+---------+
      GAGTTCGTGGTCGTGTGGCGACCTTCTTTGGTTAGACCAAGGCGACCTTTTAGGACCACG
       S   S   T   S   T   P   L   E   E   T   N   L   V   P   L   E   N   P   G   A
```

FIG. 2C

```
          ACCGGGTCCGGCAGTTCCGGGTGGTGCAGATATTAACATTAATCTGGCAATGGCCTTTGA
1081      ----------+----------+----------+----------+----------+----------+
          TGGCCCAGGCCGTCAAGGCCCACCACGTCTATAATTGTAATTAGACCGTTACCGGAAACT
           P   G   P   A   V   P   G   G   A   D   I   N   I   N   L   A   M   A   F   D

AgeI
          CGTGACCAATTTTGAACTGACCATTAACGGTAGCCCGTTTAAAGCACCGACCGCACCGGT
1141      ----------+----------+----------+----------+----------+----------+
          GCACTGGTTAAAACTTGACTGGTAATTGCCATCGGGCAAATTTCGTGGCTGGCGTGGCCA
           V   T   N   F   E   L   T   I   N   G   S   P   F   K   A   P   T   A   P   V

PstI
          TCTGCTGCAGATTCTGAGCGGTGCGACCACCGCAGCAAGCCTGCTGCCGAGCGGTAGTAT
1201      ----------+----------+----------+----------+----------+----------+
          AGACGACGTCTAAGACTCGCCACGCTGGTGGCGTCGTTCGGACGACGGCTCGCCATCATA
           L   L   Q   I   L   S   G   A   T   T   A   A   S   L   L   P   S   G   S   I

TTATAGCCTGGAAGCAAATAAAGTGGTGGAAATTAGCATTCCGGCACTGGCCGTTGGTGG
1261      ----------+----------+----------+----------+----------+----------+
          AATATCGGACCTTCGTTTATTTCACCACCTTTAATCGTAAGGCCGTGACCGGCAACCACC
           Y   S   L   E   A   N   K   V   V   E   I   S   I   P   A   L   A   V   G   G

BspMI
          TCCGCATCCGTTTCATCTGCATGGTCATACCTTTGATGTTATTCGTAGTGCAGGTAGCAC
1321      ----------+----------+----------+----------+----------+----------+
          AGGCGTAGGCAAAGTAGACGTACCAGTATGGAAACTACAATAAGCATCACGTCCATCGTG
           P   H   P   F   H   L   H   G   H   T   F   D   V   I   R   S   A   G   S   T

CACCTATAACTTTGATACACCGGCACGTCGTGATGTTGTTAATACCGGCACCGATGCAAA
1381      ----------+----------+----------+----------+----------+----------+
          GTGGATATTGAAACTATGTGGCCGTGCAGCACTACAACAATTATGGCCGTGGCTACGTTT
           T   Y   N   F   D   T   P   A   R   R   D   V   V   N   T   G   T   D   A   N

TGATAATGTGACCATTCGTTTCGTTACCGATAATCCGGGTCCGTGGTTTCTGCATTGCCA
1441      ----------+----------+----------+----------+----------+----------+
          ACTATTACACTGGTAAGCAAAGCAATGGCTATTAGGCCCAGGCACCAAAGACGTAACGGT
           D   N   V   T   I   R   F   V   T   D   N   P   G   P   W   F   L   H   C   H
```

FIG. 2D

```
              TATTGATTGGCATCTGGAAATTGGTCTGGCAGTTGTTTTTGCAGAAGATGTGACCAGCAT
       1501   ---------+---------+---------+---------+---------+---------+
              ATAACTAACCGTAGACCTTTAACCAGACCGTCAACAAAAACGTCTTCTACACTGGTCGTA
               _I__D__W__H__L__E__I__G__L__A__V__V__F__A__E__D__V__T__S__I_

TACCGCACCTCCGGCAGCATGGGATGATCTGTGCCCGATTTATGATGCACTGAGCGATTC
       1561   ---------+---------+---------+---------+---------+---------+
              ATGGCGTGGAGGCCGTCGTACCCTACTAGACACGGGCTAAATACTACGTGACTCGCTAAG
               _T__A__P__P__A__A__W__D__D__L__C__P__I__Y__D__A__L__S__D__S_

AGATAAAGGTGGTATTGCCGGTTATTATGATGATGAAGGTAGCTATCACAGCCTGAAACA
       1621   ---------+---------+---------+---------+---------+---------+
              TCTATTTCCACCATAACGGCCAATAATACTACTACTTCCATCGATAGTGTCGGACTTTGT
               _D__K__G__G__I__A__G__Y__Y__D__D__E__G__S__Y__H__S__L__K__H_

TGGTGTTGCAAAAACCATTGATAAACTGCTGCCGCATCATCACCACCATCACCATCATAG
       1681   ---------+---------+---------+---------+---------+---------+
              ACCACAACGTTTTTGGTAACTATTTGACGACGGCGTAGTAGTGGTGGTAGTGGTAGTATC
               _G__V__A__K__T__I__D__K__L__L__P__H__H__H__H__H__H__H__H__S_

BclI
              CGACCACCATCATCATTCAGATCATCATGATCACAACAACACCACCATTACCGAACATGT
       1741   ---------+---------+---------+---------+---------+---------+
              GCTGGTGGTAGTAGTAAGTCTAGTAGTACTAGTGTTGTTGTGGTGGTAATGGCTTGTACA
               _D__H__H__H__H__S__D__H__H__D__H__N__N__T__T__I__T__E__H__V_

TGAAGTTGATGTTGTGCGTCATGATGCGAATCATAGCCGTCGTGCCGCACCGGCAACCGA
       1801   ---------+---------+---------+---------+---------+---------+
              ACTTCAACTACAACACGCAGTACTACGCTTAGTATCGGCAGCACGGCGTGGCCGTTGGCT
               _E__V__D__V__V__R__H__D__A__N__H__S__R__R__A__A__P__A__T__E_

AAGCCAGCCGCAGACCGTGAGCATTCCGTGTCATCATATTCGTCTGGGTGATTTTCTGAT
       1861   ---------+---------+---------+---------+---------+---------+
              TTCGGTCGGCGTCTGGCACTCGTAAGGCACAGTAGTATAAGCAGACCCACTAAAAGACTA
               _S__Q__P__Q__T__V__S__I__P__C__H__H__I__R__L__G__D__F__L__M_
```

FIG. 2E

```
                PstI                                         AgeI
     GCTGCAGGGTCGTCCGTGTCAGGTGATTCGTATTAGCACCAGCTCAGCAACCGGTCAGTA
1921 ---------+---------+---------+---------+---------+---------+
     CGACGTCCCAGCAGGCACAGTCCACTAAGCATAATCGTGGTCGAGTCGTTGGCCAGTCAT
      L  Q  G  R  P  C  Q  V  I  R  I  S  T  S  S  A  T  G  Q  Y

HincII          PvuII
     TCGTTATCTGGGTGTTGACCTGTTTACCAAACAGCTGCATGAAGAAAGCAGCTTTATTTC
1981 ---------+---------+---------+---------+---------+---------+
     AGCAATAGACCCACAACTGGACAAATGGTTTGTCGACGTACTTCTTTCGTCGAAATAAAG
      R  Y  L  G  V  D  L  F  T  K  Q  L  H  E  E  S  S  F  I  S AAATCCGGCACCGTCAGTTGTTGTTCAGACCATGCTGGGTCCGGTTTTTAAACAGTATCG
2041 ---------+---------+---------+---------+---------+---------+
     TTTAGGCCGTGGCAGTCAACAACAAGTCTGGTACGACCCAGGCCAAAAATTTGTCATAGC
      N  P  A  P  S  V  V  V  Q  T  M  L  G  P  V  F  K  Q  Y  R AgeI
     TGTTCTGGATATGGCCGATGGTTATGTTACCGCAATGACCGAAACCGGTGATGTTAAACA
2101 ---------+---------+---------+---------+---------+---------+
     ACAAGACCTATACCGGCTACCAATACAATGGCGTTACTGGCTTTGGCCACTACAATTTGT
      V  L  D  M  A  D  G  Y  V  T  A  M  T  E  T  G  D  V  K  Q BclI                      PstI
     GGGTCTGAAAGTTATTGATCAGAGCAATCTGTGGTCACGCCTGCAGCAGGCATTTGAAAG
2161 ---------+---------+---------+---------+---------+---------+
     CCCAGACTTTCAATAACTAGTCTCGTTAGACACCAGTGCGGACGTCGTCCGTAAACTTTC
      G  L  K  V  I  D  Q  S  N  L  W  S  R  L  Q  Q  A  F  E  S PflMI
     CGGTCGTGGTAGCGTTCGCGTTCTGGTGCTGAACGATGGTGGCCATGAACTGGCGGTTGA
2221 ---------+---------+---------+---------+---------+---------+
     GCCAGCACCATCGCAAGCGCAAGACCACGACTTGCTACCACCGGTACTTGACCGCCAACT
      G  R  G  S  V  R  V  L  V  L  N  D  G  G  H  E  L  A  V  E
```

FIG. 2F

```
                                       XhoI   KpnI
       AATGAAAGTTGTTCATGGTAGCCGTCGTAACTCGAGGGTACCCTGGGCCTCATGGGCCT
2281   ---------+---------+---------+---------+---------+---------+
       TTACTTTCAACAAGTACCATCGGCAGACATTGAGCTCCCATGGGACCCGGAGTACCCGGA
        M   K   V   V   H   G   S   R   L   *

TCCTTTCACTGCCCGCTTTCCAG
2341   ---------+---------+---
       AGGAAAGTGACGGGCGAAAGGTC
```

FIG. 2G

SEQUENCE LISTING (SEQ ID NO:2)

<110> Kumar, Pratibha Vinodh and Sulaiman, Zohrah

<120> Synthetic fusion gene and its use thereof

<130> 1

<160> 1

<170> PatentIn version 3.5

<210> 1

<211> 2264

<212> DNA

<213> Synthetic fusion gene

<400> 1

| | |
|---|---|
| atgtttccag gcgcacggat tctcgctacg cttacattag ctcttcacct tttacatggg | 60 |
| actcatgctg ccattgggcc cactggcgac atgtacatcg tcaacgagga cgtctctcct | 120 |
| gacggcttca ctcgttcggc tgtcgtcgct cgctctgacc ccaccacaaa tgggacgtcg | 180 |
| gagacgctta ccggtgtcct cgtgcaagga acaagggcg acaacttcca gctgaacgtt | 240 |
| ctcaatcaac tgtcggacac gactatgttg aagaccacta gtatccattg gcatggcttc | 300 |
| tttcaatccg gttctacgtg ggcagatgga cccgcgttcg tgaatcaatg ccccatcgcc | 360 |
| tcggggaaca gcttcctata tgacttcaac gtccccgacc aagctggcac gttctggtac | 420 |
| cattcgcatc tttccaccca gtattgtgat ggtcttagag gaccattcat agtatacgac | 480 |

FIG. 3A

```
ccctccgatc cccacctgtc cttgtatgac gttgacaacg ccgacaccat cattacactt    540
gaagattggt accatgttgt ggcccctcag aatgcagtgc ttcctactgc tgatagtaca    600
ctcatcaatg gcaaaggtcg cttcgctggg gggcctactt ccgctttggc cgtcatcaac    660
gtcgaaagca acaagcgata tcgtttcaga cttatctcga tgtcttgcga ccccaatttc    720
acgttctcga tcgacggtca ctctttgcag gtcatcgagg cagacgctgt caatattgtg    780
cccattgtcg tggatagtat tcaaatcttc gcaggccaac gctattcctt cgtcttgaat    840
gccaatcaga ctgtcgacaa ttactggatt cgcgcagatc ccaacttggg atcgactggc    900
ttcgatggtg gtatcaattc cgctatcctt cggtatgctg gtgccactga agatgaccct    960
accacgactt cgtcgacgag taccccccct gaggagacta atcttgtgcc acttgaaaat    1020
cctggtgctc ctggtccagc tgtccctgga ggcgcagaca tcaacatcaa tctcgctatg    1080
gccttcgacg ttactaactt tgaactgacc atcaacggct ccccttcaa agcgccgact    1140 gctcctgttc tgctccagat tctgtcgggt gccacaactg ccgcctcact tctcccttcc    1200
ggcagtatat actcgctaga agccaacaaa gttgtcgaga tctccatacc cgccttagct    1260
gttggaggac cgcatccttt ccatcttcac ggacacacgt tcgacgtcat caggagtgcg    1320
ggctctacta cgtataactt cgacacccct gcgcgacgcg atgttgtcaa cactggaact    1380
```

FIG. 3B

```
gacgcgaacg acaacgttac tatccgctttt gtgacggata atccaggccc atggttcctc    1440
cactgccaca ttgactggca tctcgaaatc ggtcttgcgg tcgttttcgc cgaagatgtg    1500
acgtcgatca cggccccacc tgccgcgtgg gacgacttgt gtccgattta tgatgctttg    1560
agcgattccg acaaaggtgg catagcttag atgggttact acgacgacga gggctcttac    1620
cactccctca agcacggcgt cgccaagacg atcgacaagc tgctccctca tcaccaccac    1680
catcaccacc acagtgatca ccaccaccac agtgaccatc atgaccataa taacactacg    1740
atcacagagc acgttgaagt tgtgttgtcc gccacgatgc taatcactcg cgacgcgcag    1800
ctcccgccac tgagtcgcag cctcagactg tgtccatccc ctgccaccac atccgcctgg    1860
gtgacttcct gatgctccag ggccgaccat gccaggtcat ccgcatctcg acctcgtccg    1920
ccactggcca gtaccgctac cttggtgttg acctcttcac caagcagctg cacgaggagt    1980
cctccttcat ctccaaccct gcccccagcg ttgttgtcca gaccatgctc ggccccgtct    2040
tcaagcagta ccgcgtcctc gacatggctg acggctacgt caccgccatg accgagaccg    2100
gcgacgtcaa gcagggcctc aaggtcattg accagtccaa cctgtggtct cgtctgcagc    2160
aggctttcga gtccggccgc ggcagcgtcc gtgtcctggt cctcaacgac ggcggccatg    2220
```

FIG. 3C agctcgctgt tgagatgaag gtcgtccacg gctctcgcct gtaa    2264

FIG. 3D

SYNTHETIC FUSION GENE AND ITS USE THEREOF

CROSS-REFERENCE TO RELATED APPLICATIONS

The present application claims priority to Brunei Patent Application No. BN/N/2014/0037, entitled "Synthetic Fusion Gene and its use thereof" and filed on Apr. 3, 2014, the contents of which are hereby incorporated by reference.

FIELD OF THE INVENTION

The present invention relates to synthetic fusion gene comprising hex1 and pox1 genes, their process of preparation, polypeptide(s) encoded by the same and their use thereof.

BACKGROUND OF THE INVENTION

There is a growing interest in using renewable feedstock for manufacturing biofuels, such as bioethanol, biochemical and biodiesel. As such, pre-treatment of the biomass is needed to increase the rate and/or yield of biofuel production.

Currently, the main methods used for pre-treatment are physical, such as milling, or chemical, such as acid pre-treatment. However, biological methods are a promising alternative since no harmful chemicals are used and less energy input is required.

However, pre-treatment attempts to date have fallen short of the desired economic and technical performance. Thereby, there exists a need for effective, economical pre-treatments to make these polysaccharides available at a sufficiently high yield and acceptable cost.

BRIEF SUMMARY OF THE INVENTION

The present invention discloses synthetic fusion gene comprising hex1 and pox 1 genes, their process of preparation, polypeptide(s) encoded by the same and its use thereof for biological pre-treatment of biomass for the production of biodiesel.

In an embodiment, the present invention provides a polypeptide comprising an amino acid sequence of SEQ ID NO:1.

In another embodiment, it provides a polynucleotide comprising a nucleotide sequence of SEQ ID NO:2. It further describes the polynucleotide, capable of encoding a polypeptide, wherein the polypeptide comprising an amino acid sequence of SEQ ID NO. 1.

In another embodiment, the polynucleotide comprising SEQ ID NO 2 is obtained from hex 1 and pox1 gene.

In yet another embodiment, it discloses a vector comprising a polynucleotide, wherein the polynucleotide comprising a nucleotide sequence of SEQ ID NO:2.

The invention further provides a method of biological pretreatment for biofuel production comprising, introducing a vector in a host cell under conditions suitable for the expression of the vector, wherein the vector comprising a nucleotide sequence of SEQ ID NO:2 which is capable of encoding a polypeptide, the polypeptide comprising an amino acid sequence of SEQ ID NO:1.

It further discloses the method of biological pre-treatment for biofuel production, wherein the polypeptide is capable of hydrolysing lignocellulo sic biomass.

The present invention solves the long standing need of pure biological treatment, removing the need of any additional physical or chemical pre-treatment step. Further, since polynucleotide comprising a nucleotide sequence of SEQ ID NO:2 is a pure biological agent there is no hazard to the environment.

The present invention, also provides quick and cheaper method of pre-treatment of biomass as nucleotide sequence of SEQ ID NO:2 can be replicated and can be used two or more times.

BRIEF DESCRIPTION OF THE DRAWINGS

FIG. 2A shows the first part of polypeptide comprising an amino acid sequence according to the present invention encoded by the synthetic fusion gene comprising hex1 and pox1 genes. FIG. 2B shows the second part of polypeptide comprising an amino acid sequence. FIG. 2C shows the third part of polypeptide comprising an amino acid sequence. FIG. 2D shows the fourth part of polypeptide comprising an amino acid sequence. FIG. 2E shows the fifth part of polypeptide comprising an amino acid sequence. FIG. 2F shows the sixth part of polypeptide comprising an amino acid sequence. FIG. 2G shows the seventh part of polypeptide comprising an amino acid sequence. SEQ ID NO: 1 is referred by bold letter in sequence listing and SEQ ID NO: 2 is referred by light letters in sequence listing.

FIG. 3A shows the first part of polynucleotide sequence of synthetic fusion gene comprising hex1 and pox1 genes. FIG. 3B shows the second part of polynucleotide sequence of synthetic fusion gene comprising hex1 and pox1 genes. FIG. 3C shows the third part of polynucleotide sequence of synthetic fusion gene comprising hex1 and pox1 genes. FIG. 3D shows the fourth part of polynucleotide sequence of synthetic fusion gene comprising hex1 and pox1 genes. (SEQ ID NO: 2)

DEFINITIONS

Figure 1:
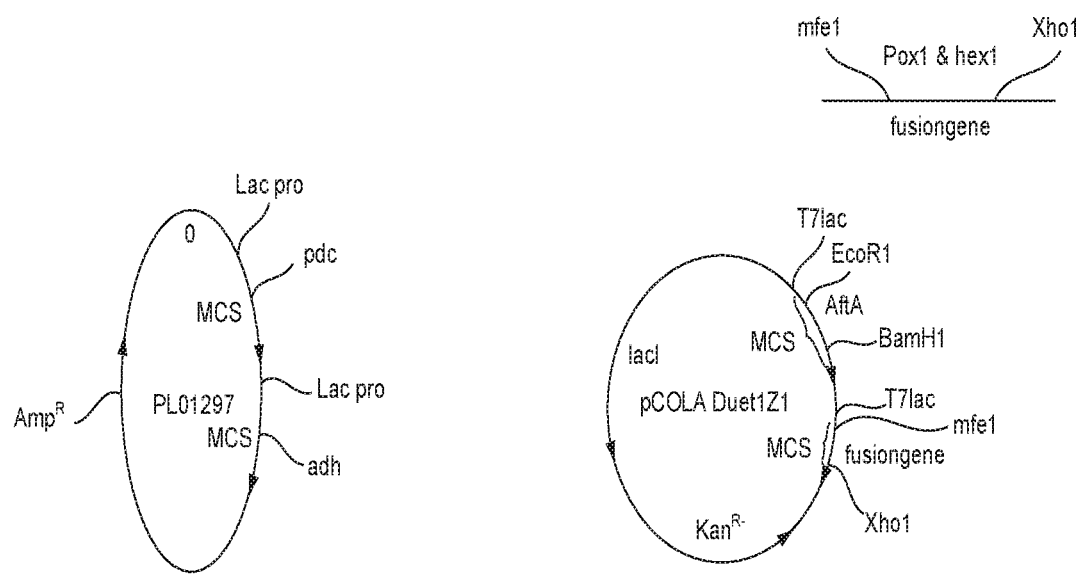
FIG. 1 shows the plasmid containing synthetic fusion gene along with biodiesel producing gene.

The term "polypeptide" corresponds to any chain of amino acids, regardless of length or post-translational modification (glycosylation or phosphorylation).

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "nucleic acid molecule" is intended to indicate any single- or double stranded nucleic acid molecule of cDNA, genomic DNA, synthetic DNA or RNA, PNAS or LNA origin.

The term "plasmid", "vector system" or "expression vector" means a construct capable of in-vivo or in-vitro expression.

The term "host cell" in relation to the present invention includes any cell that comprises either the nucleic acid molecule or an expression vector as described above and which is used in the production of polypeptide having the specific properties as defined herein or in the methods of the present invention.

DETAILED DESCRIPTION OF THE INVENTION

For the purpose of promoting and understanding of the principles of the invention, reference will now be made to embodiments and specific language will be used to describe the same. It will nevertheless be understood that no limitation of the scope of the invention is thereby intended, such alterations and further modifications in the disclosed process, and such further applications of the principles of the invention therein being contemplated as would normally occur to one skilled in the art to which the invention relates.

Reference throughout this specification to "one embodiment" "an embodiment" or similar language means that a particular feature, structure, or characteristic described in connection with the embodiment is included in at least one embodiment of the present invention. Thus, appearances of the phrase "in one embodiment", "in an embodiment" and similar language throughout this specification may, but do not necessarily, all refer to the same embodiment.

The present invention discloses synthetic fusion gene comprising hex1 and pox1 genes, their process of preparation, polypeptide(s) encoded by the same and its use thereof for biological pre-treatment of biomass for the production of biodiesel.

The invention further discloses that the synthetic fusion gene was constructed using bioinformatics tools to help complete hydrolysis of lignocelluloses of Laila paddy into glucose for the production of biodiesel from (husk/straw) of Laila paddy.

The present disclosure relates to a polypeptides comprising an amino acid sequence of SEQ ID NO: 1 as referred by bold letter in sequence listing of FIG. 2A, FIG. 2B, FIG. 2C, FIG. 2D, FIG. 2E, FIG. 2F, and FIG. 2G.

In another aspect, the disclosure provides a polynucleotide comprising a nucleotide sequence of SEQ ID NO:2. It further describes the polynucleotide, capable of encoding a polypeptide, wherein the polypeptide comprising an amino acid sequence of SEQ ID NO: 1.

In further discloses that, the polynucleotide comprising SEQ ID NO: 2 is obtained from hex1 and pox1 gene.

In order to produce a polypeptide, it discloses a vector comprising a polynucleotide, wherein the polynucleotide comprising a nucleotide sequence of SEQ ID NO: 2.

The invention further provides a method of biological pre-treatment for biofuel production, wherein the polynucleotide comprising SEQ ID NO: 2 is included in an expression cassette and/or cloned into a suitable expression vector by standard molecular cloning techniques. The expression cassette or vector is introduced into a suitable expression host cell, which then expresses the corresponding polypeptide comprising SEQ ID NO: 1.

It further discloses the method of biological pre-treatment for biofuel production, wherein the polypeptide is capable of hydrolysing lignocellulosic biomass.

The present invention solves the long standing need of pure biological treatment, removing the need of any additional physical or chemical pre-treatment step. Further, since polynucleotide comprising a nucleotide sequence of SEQ ID NO:2 is a pure biological agent there is no hazard to the environment.

The present invention, also provides quick and cheaper method of pre-treatment of biomass as nucleotide sequence of SEQ ID NO: 2 can be replicated and can be used two or more times.

In an embodiment, the present invention arranges synthetic fusion gene to help complete hydrolysis of lignocelluloses of Laila paddy into glucose for production of biodiesel from hust/straw of laila paddy. The invention arranges Hex 1 and Pox1. Hex1 is a fungi which is mainly used for hydrolysis of cellulose and hemicelluloses in pretreatment. Pox1 is a mushroom which is used to break down lignin in lignocelluloses. The invention joins Hex1 and Pox1 together by arranging their cDNA nucleotides to construct new synthetic fusion gene.

In another embodiment, end codon of *Tricoderma reesei* (hex 1) is spliced and start codon of *Pleurotus sojar caju* (pox1) is attached to it by synthetic arrangement of nucleotides. *Pleurotus sojar cajus* (pox1) stop codon act as end codons for both genes. Therefore, fusion gene work as a single gene having both properties of hex 1 and pox 1.

For any Production of Biodiesel/micro diesel from ligno cellulose (Cellulose, hemicellulose & lignin) it is necessary to do a pre-treatment. However, no additional pretreatment process is required when novel fusion gene is used and fermentation step can be carried out without pretreatment. Synthetic fusion gene can be placed in same plasmid along with other gene used for production of biodiesel.

A Pre-treatment is a phase in which the lignocelluloses materials such as wood or straw is amenable to hydrolysis. Pre-treatment technique has been generally divided into physical, chemical and biological. Physical Treatment includes Milling and Grinding, Chemical Treatment includes Using Acids or alkali, and Biological Treatment includes mostly using Rot Fungi in combination with Physical treatment. However using the synthetic gene there is no need for a pre-treatment as the fusion gene is placed in the same plasmid along with biodiesel producing gene. Hence, hydrolysis of ligno cellulose takes place along with biodiesel production during fermentation.

Generally lignocelluloses has to undergo first a Combined pretreatment (Physical, Chemical, and an expensive Enzymatic treatment) prior to fermentation process. However the pre-treatment does not break the lignin or through some enzymes only partial breakdown of lignin is achieved. Thus a major part of lignin remain intact which is also a carbon source that is wasted. The present invention is a one step process in which invitro enzymatic pretreatment resulting from fusion gene hex1pox1 & fermentation takes place in the same medium. Also complete breakdown of lignin is achieved thereby increasing the production of biodiesel as all sources of carbon from lignocelluloses are utilized.

In another embodiment, Aerobic Fermentation was used. Fermentation flask was immersed in a temperature controlled water bath maintained at 37° C. and stirred at 250-280 rpm for 24 hours. pH was maintained within the range of 6.8 to 7. Lower temperatures upto 30 deg C. was tried, the growth of bacteria was not seen in the medium. Higher temperature yielded a turbid medium within 6 hours indicating full growth however resulted a very low yield. Thus 37 deg C. was the optimal temperature which resulted in the best yield.

The synthetic fusion gene comprises of hex1 and pox1 gene by synthetic arrangement of nucleotides, wherein hex1 and pox1 helps in hydrolysis of cellulose, hemicelluloses and lignin. The synthetic fusion gene helps in complete hydrolysis of lignocellulose into glucose without the use of any pre-treatment method for biodiesel production from paddy.

In another embodiment, the synthetic fusion gene can also be used as a pure biological pre-treatment tool for any production of micro diesel. The Synthetic gene is also used in p Cola duet 1 Z.

In another embodiment Genes hex1 and pox1 play the role of degradation of lignocellulose.

In an embodiment, the invention may be used on Biomass to produce biofuel. The biomass includes Laila paddy, husk and straw. *Oriza sativa* having same chemical component or any lignocellulose biomass having same component with different ratio can also be used as biomass.

In an embodiment, Fad E. del *E. coli* is used as host organism. Gene is optimized for *E. coli*. For other host organism like mammalian, insect and yeast expression a KOZAK sequence is recommended to the upstream of the construct.

In another embodiment, other gene that are combined with pox1 hex1 are pdc, adh, and aft A. pdc & adh help in production of ethanol and aft A helps in the conversion of ethanol into biodiesel). Thus these gene (pdc, adh, aft A) complement fusion gene in producing biodiesel not in any hydrolytic process of lignocellulose.

Construction of Synthetic Fusion Gene:

*Tricoderma reesei* (hex1) is a fungi which is mainly used for hydrolysis of cellulose and hemicelluloses in pre-treatment and *Pleurotous sojar caju* (pox1) is a mushroom which is used to breakdown lignin in lignocelluloses. These two particular genes hex1 and pox1 play the role of degradation in these fungi. In the present invention, hex 1 and pox1 were joined together by arranging their cDNA nucleotides, to construct new synthetic fusion gene. Here end codon of *Tricoderma reesei* (hex 1) was spiked and *Pleurotous sojar caju* (pox1) start codon was attached to it by synthetic arrangement of nucleotides. The stop codon of *Pleurotous sojar caju* (pox 1) acts as end codons for both the genes. Thus, the fusion gene works as single gene having both properties.

SPECIFIC EMBODIMENTS ARE DESCRIBED BELOW

A polypeptide comprising an amino acid sequence of SEQ ID NO: 1 as referred by bold letter in sequence listing of FIG. 2A, FIG. 2B, FIG. 2C, FIG. 2D, FIG. 2E, FIG. 2F, and FIG. 2G.

FURTHER SPECIFIC EMBODIMENTS ARE DESCRIBED BELOW

A polynucleotide comprising a nucleotide sequence of SEQ ID NO: 2 as referred by light letter in sequence listing of FIG. 2A, FIG. 2B, FIG. 2C, FIG. 2D, FIG. 2E, FIG. 2F, and FIG. 2G.

Such polynucleotide(s), capable of encoding a polypeptide, the polypeptide comprising an amino acid sequence of SEQ ID NO. 1.

Such polynucleotide(s), wherein the SEQ ID NO 2 is obtained from hex1 and pox1 gene.

FURTHER SPECIFIC EMBODIMENTS ARE DESCRIBED BELOW

A vector comprising a polynucleotide, the polynucleotide comprising a nucleotide sequence of SEQ ID NO: 2.

FURTHER SPECIFIC EMBODIMENTS ARE DESCRIBED BELOW

A method of biological pre-treatment for biofuel production comprising: introducing a vector in a host cell under conditions suitable for the expression of the vector, wherein the vector comprising a nucleotide sequence of SEQ ID NO:2 which is capable of encoding a polypeptide, the polypeptide comprising an amino acid sequence of SEQ ID NO:1.

Such method(s), wherein the polypeptide is capable of hydrolysing lignocellulosic biomass.

INDUSTRIAL APPLICABILITY

The present invention discloses the method of biological pre-treatment for biofuel production, wherein the polypeptide is capable of hydrolysing lignocellulosic biomass.

Further, the present invention solves the long standing need of pure biological treatment, removing the need of any additional physical or chemical pre-treatment step. Further, since polynucleotide comprising a nucleotide sequence of SEQ ID NO: 2 is a pure biological agent there is no hazard to the environment.

Furthermore, the present invention, also provides quick and cheaper method of pre-treatment of biomass as nucleotide sequence of SEQ ID NO: 2 can be replicated and can be used two or more times

SEQUENCE LISTING

```
<160> NUMBER OF SEQ ID NOS: 3

<210> SEQ ID NO 1
<211> LENGTH: 752
<212> TYPE: PRT
<213> ORGANISM: Artificial Sequence
<220> FEATURE:
<223> OTHER INFORMATION: Synthetic Fusion

<400> SEQUENCE: 1

Met Phe Pro Gly Ala Arg Ile Leu Ala Thr Leu Thr Leu Ala Leu His
1               5                   10                  15

Leu Leu His Gly Thr His Ala Ala Ile Gly Pro Thr Gly Asp Met Tyr
                20                  25                  30

Ile Val Asn Glu Asp Val Ser Pro Asp Gly Phe Thr Arg Ser Ala Val
            35                  40                  45

Val Ala Arg Ser Asp Pro Thr Thr Asn Gly Thr Ser Glu Thr Leu Thr
        50                  55                  60

Gly Val Leu Val Gln Gly Asn Lys Gly Asp Asn Phe Gln Leu Asn Val
65                  70                  75                  80
```

```
Leu Asn Gln Leu Ser Asp Thr Thr Met Leu Lys Thr Ser Ile His
                85                  90                  95

Trp His Gly Phe Phe Gln Ser Gly Ser Thr Trp Ala Asp Gly Pro Ala
            100                 105                 110

Phe Val Asn Gln Cys Pro Ile Ala Ser Gly Asn Ser Phe Leu Tyr Asp
            115                 120                 125

Phe Asn Val Pro Asp Gln Ala Gly Thr Phe Trp Tyr His Ser His Leu
130                 135                 140

Ser Thr Gln Tyr Cys Asp Gly Leu Arg Gly Pro Phe Ile Val Tyr Asp
145                 150                 155                 160

Pro Ser Asp Pro His Leu Ser Leu Tyr Asp Val Asp Asn Ala Asp Thr
                165                 170                 175

Ile Ile Thr Leu Glu Asp Trp Tyr His Val Val Ala Pro Gln Asn Ala
            180                 185                 190

Val Leu Pro Thr Ala Asp Ser Thr Leu Ile Asn Gly Lys Gly Arg Phe
            195                 200                 205

Ala Gly Gly Pro Thr Ser Ala Leu Ala Val Ile Asn Val Glu Ser Asn
            210                 215                 220

Lys Arg Tyr Arg Phe Arg Leu Ile Ser Met Ser Cys Asp Pro Asn Phe
225                 230                 235                 240

Thr Phe Ser Ile Asp Gly His Ser Leu Gln Val Ile Glu Ala Asp Ala
                245                 250                 255

Val Asn Ile Val Pro Ile Val Val Asp Ser Ile Gln Ile Phe Ala Gly
                260                 265                 270

Gln Arg Tyr Ser Phe Val Leu Asn Ala Asn Gln Thr Val Asp Asn Tyr
            275                 280                 285

Trp Ile Arg Ala Asp Pro Asn Leu Gly Ser Thr Gly Phe Asp Gly Gly
            290                 295                 300

Ile Asn Ser Ala Ile Leu Arg Tyr Ala Gly Ala Thr Glu Asp Asp Pro
305                 310                 315                 320

Thr Thr Thr Ser Ser Thr Ser Thr Pro Leu Glu Glu Thr Asn Leu Val
                325                 330                 335

Pro Leu Glu Asn Pro Gly Ala Pro Gly Pro Ala Val Pro Gly Gly Ala
            340                 345                 350

Asp Ile Asn Ile Asn Leu Ala Met Ala Phe Asp Val Thr Asn Phe Glu
            355                 360                 365

Leu Thr Ile Asn Gly Ser Pro Phe Lys Ala Pro Thr Ala Pro Val Leu
            370                 375                 380

Leu Gln Ile Leu Ser Gly Ala Thr Ala Ala Ser Leu Leu Pro Ser
385                 390                 395                 400

Gly Ser Ile Tyr Ser Leu Glu Ala Asn Lys Val Val Glu Ile Ser Ile
            405                 410                 415

Pro Ala Leu Ala Val Gly Gly Pro His Pro Phe His Leu His Gly His
            420                 425                 430

Thr Phe Asp Val Ile Arg Ser Ala Gly Ser Thr Thr Tyr Asn Phe Asp
        435                 440                 445

Thr Pro Ala Arg Arg Asp Val Val Asn Thr Gly Thr Asp Ala Asn Asp
450                 455                 460

Asn Val Thr Ile Arg Phe Val Thr Asp Asn Pro Gly Pro Trp Phe Leu
465                 470                 475                 480

His Cys His Ile Asp Trp His Leu Glu Ile Gly Leu Ala Val Val Phe
                485                 490                 495
```

```
Ala Glu Asp Val Thr Ser Ile Thr Ala Pro Pro Ala Ala Trp Asp Asp
            500                 505                 510

Leu Cys Pro Ile Tyr Asp Ala Leu Ser Asp Ser Asp Lys Gly Gly Ile
        515                 520                 525

Ala Gly Tyr Tyr Asp Asp Glu Gly Ser Tyr His Ser Leu Lys His Gly
    530                 535                 540

Val Ala Lys Thr Ile Asp Lys Leu Leu Pro His His His His His
545                 550                 555                 560

His His Ser Asp His His His Ser Asp His Asp His Asn Asn
                565                 570                 575

Thr Thr Ile Thr Glu His Val Glu Val Asp Val Val Arg His Asp Ala
            580                 585                 590

Asn His Ser Arg Arg Ala Ala Pro Ala Thr Glu Ser Gln Pro Gln Thr
            595                 600                 605

Val Ser Ile Pro Cys His His Ile Arg Leu Gly Asp Phe Leu Met Leu
        610                 615                 620

Gln Gly Arg Pro Cys Gln Val Ile Arg Ile Ser Thr Ser Ser Ala Thr
625                 630                 635                 640

Gly Gln Tyr Arg Tyr Leu Gly Val Asp Leu Phe Thr Lys Gln Leu His
            645                 650                 655

Glu Glu Ser Ser Phe Ile Ser Asn Pro Ala Pro Ser Val Val Val Gln
            660                 665                 670

Thr Met Leu Gly Pro Val Phe Lys Gln Tyr Arg Val Leu Asp Met Ala
        675                 680                 685

Asp Gly Tyr Val Thr Ala Met Thr Glu Thr Gly Asp Val Lys Gln Gly
    690                 695                 700

Leu Lys Val Ile Asp Gln Ser Asn Leu Trp Ser Arg Leu Gln Gln Ala
705                 710                 715                 720

Phe Glu Ser Gly Arg Gly Ser Val Arg Val Leu Val Leu Asn Asp Gly
                725                 730                 735

Gly His Glu Leu Ala Val Glu Met Lys Val Val His Gly Ser Arg Leu
            740                 745                 750

<210> SEQ ID NO 2
<211> LENGTH: 2264
<212> TYPE: DNA
<213> ORGANISM: Artificial Sequence
<220> FEATURE:
<223> OTHER INFORMATION: Synthetic Fusion

<400> SEQUENCE: 2
atgtttccag gcgcacggat tctcgctacg cttacattag ctcttcacct tttacatggg        60
actcatgctg ccattgggcc cactggcgac atgtacatcg tcaacgagga cgtctctcct       120
gacggcttca ctcgttcggc tgtcgtcgct cgctctgacc ccaccacaaa tgggacgtcg       180
gagacgctta ccggtgtcct cgtgcaagga aacaagggcg acaacttcca gctgaacgtt       240
ctcaatcaac tgtcggacac gactatgttg aagaccacta gtatccattg gcatggcttc       300
tttcaatccg gttctacgtg ggcagatgga cccgcgttcg tgaatcaatg ccccatcgcc       360
tcggggaaca gcttcctata tgacttcaac gtccccgacc aagctggcac gttctggtac       420
cattcgcatc tttccacccca gtattgtgat ggtcttagag gaccattcat agtatacgac       480
ccctccgatc ccacacctgtc cttgtatgac gttgacaacg ccgacaccat cattacactt       540
gaagattggt accatgttgt ggcccctcag aatgcagtgc ttcctactgc tgatagtaca       600
ctcatcaatg gcaaaggtcg cttcgctggg gggcctactt ccgctttggc cgtcatcaac       660
```

```
gtcgaaagca acaagcgata tcgtttcaga cttatctcga tgtcttgcga ccccaatttc      720
acgttctcga tcgacggtca ctctttgcag gtcatcgagg cagacgctgt caatattgtg      780
cccattgtcg tggatagtat tcaaatcttc gcaggccaac gctattcctt cgtcttgaat      840
gccaatcaga ctgtcgacaa ttactggatt cgcgcagatc ccaacttggg atcgactggc      900
ttcgatggtg gtatcaattc cgctatcctt cggtatgctg gtgccactga agatgaccct      960
accacgactt cgtcgacgag taccccccctt gaggagacta tcttgtgcc acttgaaaat     1020 cctggtgctc ctggtccagc tgtccctgga ggcgcagaca tcaacatcaa tctcgctatg     1080
gccttcgacg ttactaactt tgaactgacc atcaacggct cccccttcaa agcgccgact     1140
gctcctgttc tgctccagat tctgtcgggt gccacaactg ccgcctcact tctcccttcc     1200
ggcagtatat actcgctaga agccaacaaa gttgtcgaga tctccatacc cgccttagct     1260
gttggaggac cgcatccttt ccatcttcac ggacacacgt tcgacgtcat caggagtgcg     1320
ggctctacta cgtataactt cgacacccct gcgcgacgcg atgttgtcaa cactggaact     1380
gacgcgaacg acaacgttac tatccgcttt gtgacggata tccaggccc atggttcctc      1440 cactgccaca ttgactggca tctcgaaatc ggtcttgcgg tcgttttcgc cgaagatgtg     1500
acgtcgatca cggccccacc tgccgcgtgg gacgacttgt gtccgattta tgatgctttg     1560
agcgattccg acaaaggtgg catagcttag atgggttact cgacgacga gggctcttac      1620 cactccctca agcacggcgt cgccaagacg atcgacaagc tgctccctca tcaccaccac     1680
catcaccacc acagtgatca ccaccaccac agtgaccatc atgaccataa taacactacg     1740
atcacagagc acgttgaagt tgtgttgtcc gccacgatgc taatcactcg cgacgcgcag     1800
ctcccgccac tgagtcgcag cctcagactg tgtccatccc ctgccaccac atccgcctgg     1860
gtgacttcct gatgctccag ggccgaccat gccaggtcat ccgcatctcg acctcgtccg     1920
ccactggcca gtaccgctac cttggtgttg acctcttcac caagcagctg cacgaggagt     1980
cctccttcat ctccaaccct gcccccagcg ttgttgtcca gaccatgctc ggccccgtct     2040
tcaagcagta ccgcgtcctc gacatggctg acggctacgt caccgccatg accgagaccg     2100
gcgacgtcaa gcagggcctc aaggtcattg accagtccaa cctgtggtct cgtctgcagc     2160
aggctttcga gtccggccgc ggcagcgtcc gtgtcctggt cctcaacgac ggcggccatg     2220
agctcgctgt tgagatgaag gtcgtccacg gctctcgcct gtaa                      2264
```

<210> SEQ ID NO 3
<211> LENGTH: 2363
<212> TYPE: DNA
<213> ORGANISM: Artificial Sequence
<220> FEATURE:
<223> OTHER INFORMATION: Synthetic Fusion

<400> SEQUENCE: 3

```
cactataggg cgaattgaag gaaggccgtc aaggccgcat gagctccaat tgatgtttcc       60
gggtgcacgt attctggcaa ccctgaccct ggcactgcat ctgctgcatg cacccatgc      120 agccattggt ccgaccggtg atatgtatat tgttaacgaa gatgttagtc cggatggttt      180
tacccgtagc gcagttgttg cacgtagcga tccgaccacc aatggcacca gcgaaaccct      240
gacaggtgtt ctggttcagg gtaataaagg tgataatttc cagctgaatg tgctgaatca      300
gctgagcgat accaccatgc tgaaaaccac cagtattcat tggcatggtt ttttcagag      360 cggtagcacc tgggcagatg gtccggcatt tgttaatcag tgtccgattg caagcggtaa      420
```

-continued

```
cagctttctg tatgatttta atgttccgga tcaggcaggc accttttggt atcatagcca   480
tctgagcacc cagtattgtg atggtctgcg tggtccgttt attgtttatg atccgagcga   540
tccgcatctg agcctgtatg atgttgataa tgcagatacc attatcaccc tggaagattg   600
gtatcacgtt gtggcaccgc agaatgccgt tctgccgacc gcagatagca ccctgattaa   660
tggtaaaggt cgttttgcag gcggtccgac cagcgcactg gcagttatta atgttgaaag   720
caataaacgc tatcgctttc gcctgattag catgagctgt gatccgaact ttacctttag   780
cattgatggt catagcctgc aggttattga agcagatgcc gttaatattg ttccgattgt   840
tgttgatagc atccagattt ttgcaggtca gcgttatagc tttgttctga atgcaaatca   900
gaccgtggat aactattgga ttcgtgcaga tccgaatctg ggtagcaccg gttttgatgg   960
tggcattaat agcgcaattc tgcgttatgc cggtgcaacc gaagatgatc cgacaaccac  1020
ctcaagcacc agcacaccgc tggaagaaac caatctggtt ccgctggaaa atcctggtgc  1080
accgggtccg gcagttccgg gtggtgcaga tattaacatt aatctggcaa tggccttt ga  1140 cgtgaccaat tttgaactga ccattaacgg tagcccgttt aaagcaccga ccgcaccggt  1200
tctgctgcag attctgagcg gtgcgaccac cgcagcaagc ctgctgccga gcggtagtat  1260
ttatagcctg gaagcaaata agtggtgga aattagcatt ccggcactgg ccgttggtgg  1320
tccgcatccg tttcatctgc atggtcatac ctttgatgtt attcgtagtg caggtagcac  1380
cacctataac tttgatacac cggcacgtcg tgatgttgtt aataccggca ccgatgcaaa  1440
tgataatgtg accattcgtt tcgttaccga taatccgggt ccgtggtttc tgcattgcca  1500
tattgattgg catctggaaa ttggtctggc agttgttttt gcagaagatg tgaccagcat  1560
taccgcacct ccggcagcat gggatgatct gtgcccgatt tatgatgcac tgagcgattc  1620
agataaaggt ggtattgccg ttattatga tgatgaaggt agctatcaca gcctgaaaca  1680
tggtgttgca aaaaccattg ataaactgct gccgcatcat caccaccatc accatcatag  1740
cgaccaccat catcattcag atcatcatga tcacaacaac accaccatta ccgaacatgt  1800
tgaagttgat gttgtgcgtc atgatgcgaa tcatagccgt cgtgccgcac cggcaaccga  1860
aagccagccg cagaccgtga gcattccgtg tcatcatatt cgtctgggtg attttctgat  1920
gctgcagggt cgtccgtgtc aggtgattcg tattagcacc agctcagcaa ccggtcagta  1980
tcgttatctg ggtgttgacc tgtttaccaa acagctgcat gaagaaagca gctttatttc  2040
aaatccggca ccgtcagttg ttgttcagac catgctgggt ccggttttta aacagtatcg  2100
tgttctggat atggccgatg gttatgttac cgcaatgacc gaaaccggtg atgttaaaca  2160
gggtctgaaa gttattgatc agagcaatct gtggtcacgc ctgcagcagg catttgaaag  2220
cggtcgtggt agcgttcgcg ttctggtgct gaacgatggt ggccatgaac tggcggttga  2280
aatgaaagtt gttcatggta gccgtctgta actcgagggt accctgggcc tcatgggcct  2340
tcctttcact gcccgctttc cag                                         2363
```

What is claimed is:

1. A polypeptide comprising the amino acid sequence of SEQ ID NO:1, wherein the polypeptide is capable of hydrolysing lignocellulosic biomass.

2. A polynucleotide comprising the nucleotide sequence of SEQ ID NO:2.

3. The polynucleotide as claimed in claim 2, capable of encoding the polypeptide, the polypeptide comprising amino acid sequence of SEQ ID NO: 1.

4. The polynucleotide as claimed in claim 2, wherein the SEQ ID NO: 2 is obtained from *Tricoderma reesei* (hex 1) and *Pleurotous sojar caju* (pox 1) gene.

5. A synthetic fusion gene comprising *Tricoderma reesei* (hex1) and *Pleurotous sojar caju* (pox1) wherein the hex1 and the pox1 are joined together by arranging their cDNA nucleotides.

6. The synthetic fusion gene of claim 5 wherein:
end codon of the hex1 is spliced and start codon of the pox1 is attached to the spliced end condon of the hex 1 by synthetic arrangement of nucleotides.

* * * * *